United States Patent [19]

Irwin

[11] Plant 4,066

[45] June 28, 1977

[54] KALANCHOE PLANT

[76] Inventor: Lawrence T. Irwin, P.O. Box 657, Canyon, Tex. 79015

[21] Appl. No.: 693,881

[22] Filed: June 7, 1976

[51] Int. Cl.[2] ..... A01H 5/00

[52] U.S. Cl. ..... Plt./68

[58] Field of Search ..... Plt./68

*Primary Examiner*—Robert E. Bagwill

*Attorney, Agent, or Firm*—Frank B. Robb

EXEMPLARY CLAIM

1. A new and distinct variety of Kalanchoe plant, substantially as herein shown and described, characterized particularly as to novelty by the unique combination of its orange red color with a distinctive yellow eye; medium large sized flexible foilage of fern green color; its tall habit of from 16 inches to 20 inches in height; the profusion of flowers carried on sturdy stems 6 inches above the foliage; and its adaptability to year round flowering by photoperiod manipulation.

1 Drawing Figure

The present invention relates to a new and distinct variety of Kalanchoe plant which was originated by me by crossing the Kalanchoe variety known as "Exotic" (U.S. Plant Pat. No. 3,149) with an unpatented variety known as "Ramona", the former being the seed parent and the latter being the pollen parent.

As the result of this breeding, I have produced a new and improved Kalanchoe variety which is distinguished from its parents, as well as from all other Kalanchoe varieties of which I am aware, as evidenced by the following unique combination of principal characteristics which are outstanding in the new variety and which make it a valuable addition to the line of Kalanchoe varieties which are presently commercially available:

1. Its unique orange red color with a yellow eye;
2. Medium large size flexible foliage of fern green color;
3. Its tall habit, from 16 inches to 20 inches in height;
4. The profusion of flowers carried on a sturdy stem 6 inches above the foliage;
5. Its adaptability to year round flowering controlled by photoperiod manipulation.

Asexual reproduction of my new Kalanchoe variety by means of cuttings performed by me in my greenhouse located at Canyon, Tex., shows that the foregoing characteristics and distinctions come true and are established and transmitted through succeeding propagations.

The accompanying drawing shows a typical blooming plant of my new variety, and in addition a close up view of the flowers, as depicted in color, being nearly as true as is possible to make the same in a color illustration of this character.

There follows a detailed description of my new variety, with color terminology in accordance with Maerz and Paul Dictionary of Color, Exotica No. 3 by A. B. Graf, except where general color terms of ordinary dictionary significance are appropriate:

Parentage: Seedling.

*Seed parent.*—"Exotic" (U.S. Plant Pat. No. 3,149).

*Pollen parent.*—"Ramona" an unnamed hybrid.

Propagation: Holds its distinguishing characteristics through succeeding propagations by cuttings.

Locality where grown and observed: Canyon, Tex.

Plant:

*Form.*—Tall; much branched; upright.

*Growth habit.*—Medium vigorous; upright branching 16 inches to 20 inches tall.

*Rooting habit.*—Coordinate; roots easily from any part of the stem forming a fibrous root system.

*Blooming habit.*—Natural flowering occurs approximately December 15th as it is a short day plant.

*Blooming season.*—Its short day response to flowering may be used to bring the plant into bloom the year round by appropriate photoperiodic manipulation; normally blooms in about 12 weeks.

Foliage:

*Size.*—Large.

*Quantity.*—Abundant.

*Color.*—New foliage — Upper side — (83) Fern Green; Under side — (83−). Old foliage — Upper side — (83+); Under side — (83).

*Shape.*—Somewhat oval obtuse.

*Texture.*—Upper side — Glossy and smooth. Under side — Smooth.

Disease resistance: Equally as resistant to diseases as other new varieties and much more resistant than older standard varieties, as determined by comparison with other varieties in the greenhouse at Canyon, Tex.

Flowers: Pistillate staminate.

*Size.*—Diameter — 1.5 cm. Depth — 1.25 cm.

*Petals.*—Length — 0.7 cm. Width — About 0.6 cm.

*Form.*—Umbel.

*Color.*—Upper side — New flowers — (25+32); Old flowers — More Scarlet (25). Lower side — (31−) Throat of corolla — A distinct yellow eye (4−).

*Blooming period.*—About 4 to 5 weeks.

Fruit: None.

Hardiness: A range of 50° F to 100° F in the greenhouse indicates that the plant has no problem in this respect.

General observations: This new variety has the distinctive desirable qualities of a good pot plant with vigorous growth, good color and upright form making it distinctive from all other Kalanchoes. The fact that it will flower in 12 weeks and that one cutting makes a large pot are other unique aspects distinctive from other Kalanchoe varieties.

I claim:

1. A new and distinct variety of Kalanchoe plant, substantially as herein shown and described, characterized particularly as to novelty by the unique combination of its orange red color with a distinctive yellow eye; medium large sized flexible foliage of fern green color; its tall habit of from 16 inches to 20 inches in height; the profusion of flowers carried on sturdy stems 6 inches above the foliage; and its adaptability to year round flowering by photoperiod manipulation.

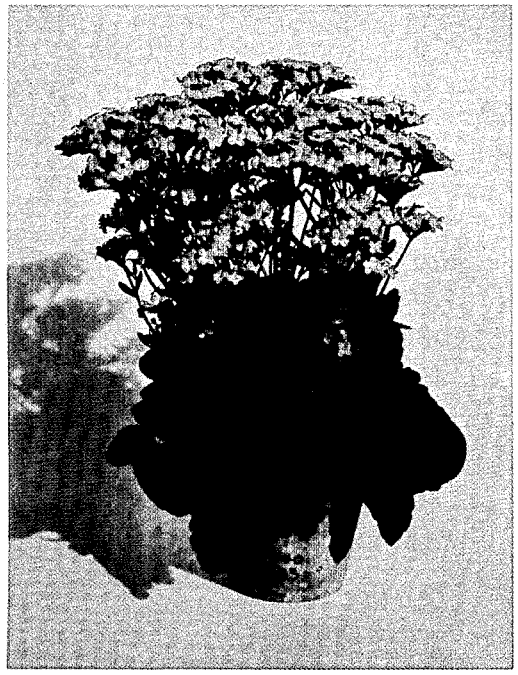
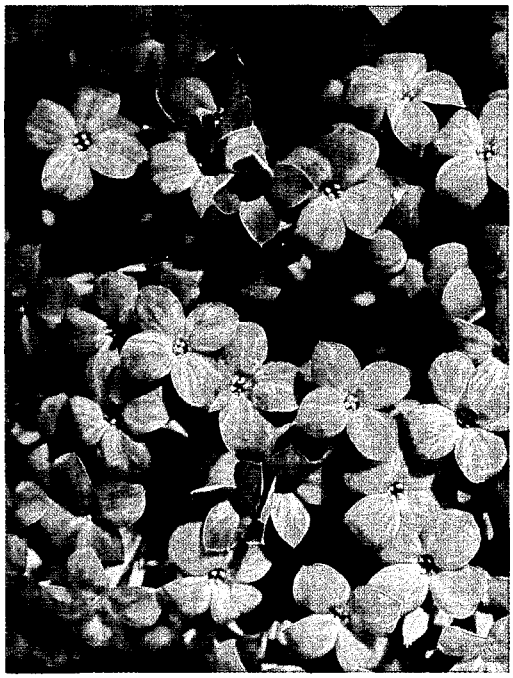

* * * * *